United States Patent [19]

Scheller et al.

[11] Patent Number: 4,773,897
[45] Date of Patent: Sep. 27, 1988

[54] COLLECTION CONTAINER FOR OPHTHALMIC SURGICAL SYSTEM

[75] Inventors: Gregg Scheller; Jerry Gahn, both of Ballwin; James Easley, Bridgeton, all of Mo.

[73] Assignee: Storz Instrument Company, St. Louis, Mo.

[21] Appl. No.: 928,265

[22] Filed: Nov. 6, 1986

[51] Int. Cl.$^4$ .............................................. A61M 1/00
[52] U.S. Cl. .................................... 604/34; 604/250; 604/317
[58] Field of Search ................. 604/317–321, 604/27, 31, 34, 48, 246–250; 433/91, 92, 95

[56] References Cited

U.S. PATENT DOCUMENTS 4,444,548  4/1984  Anderson et al. ................. 604/317
4,475,904  10/1984  Wang ................................. 604/119
4,626,248  12/1986  Scheiler ............................. 604/319

FOREIGN PATENT DOCUMENTS 8606964  12/1986  PCT Int'l Appl. ................... 604/30

Primary Examiner—C. Fred Rosenbaum
Assistant Examiner—J. L. Kruter
Attorney, Agent, or Firm—Harness, Dickey & Pierce

[57] ABSTRACT

The collection container has a reusable, autoclavable vessel with a resilient plastic reusable insert to which the aspiration instrument is connected. The insert incorporates a fluid passageway which may be blocked by squeezing action of a solenoid-type actuator. The insert includes a breakaway portion which is severed from the body of the insert during installation prior to use. This insert may also stay in place during autoclaving or cleaning.

21 Claims, 4 Drawing Sheets

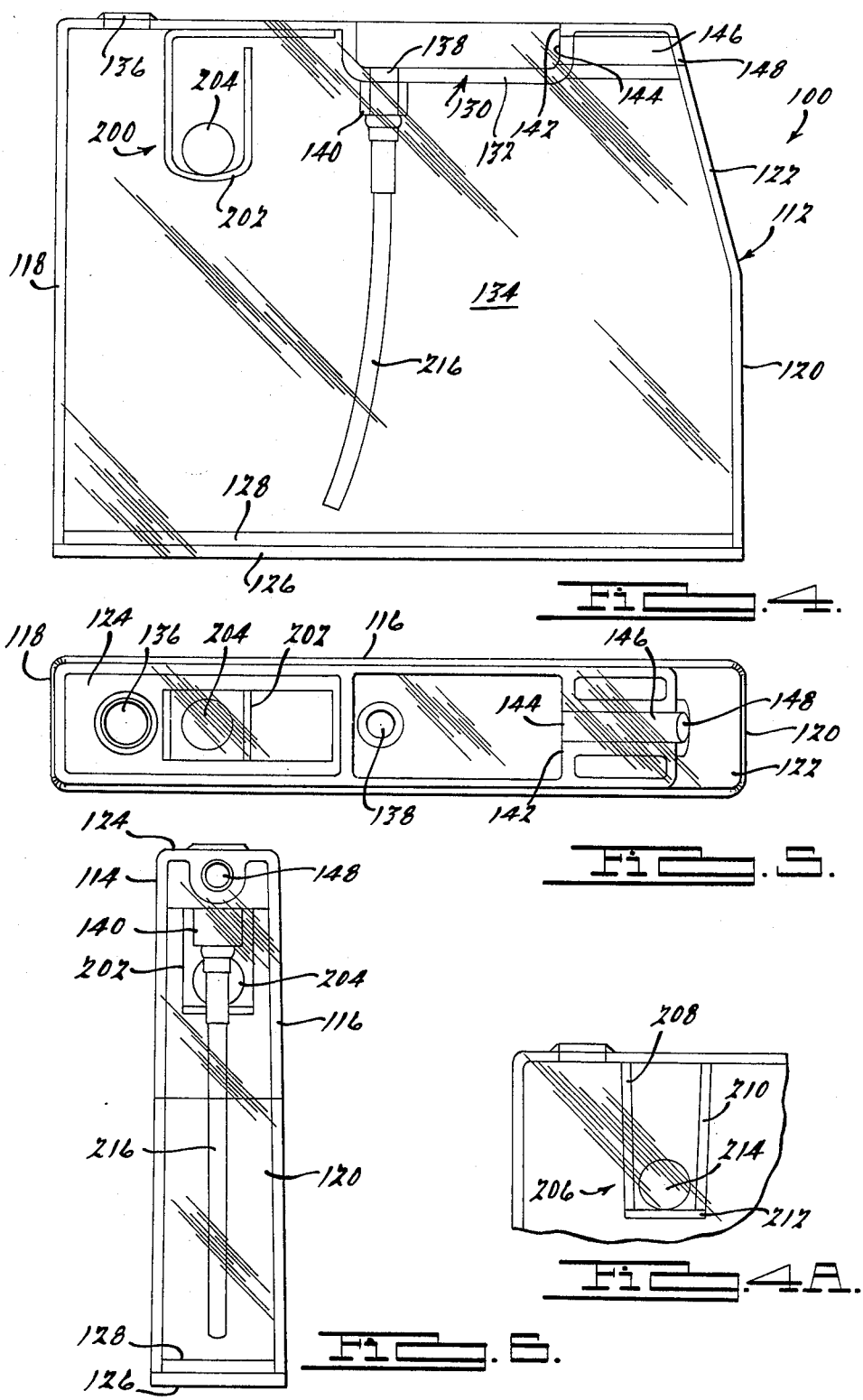

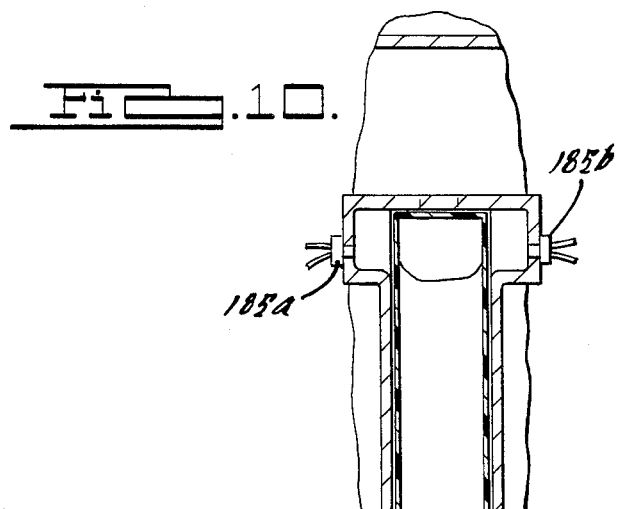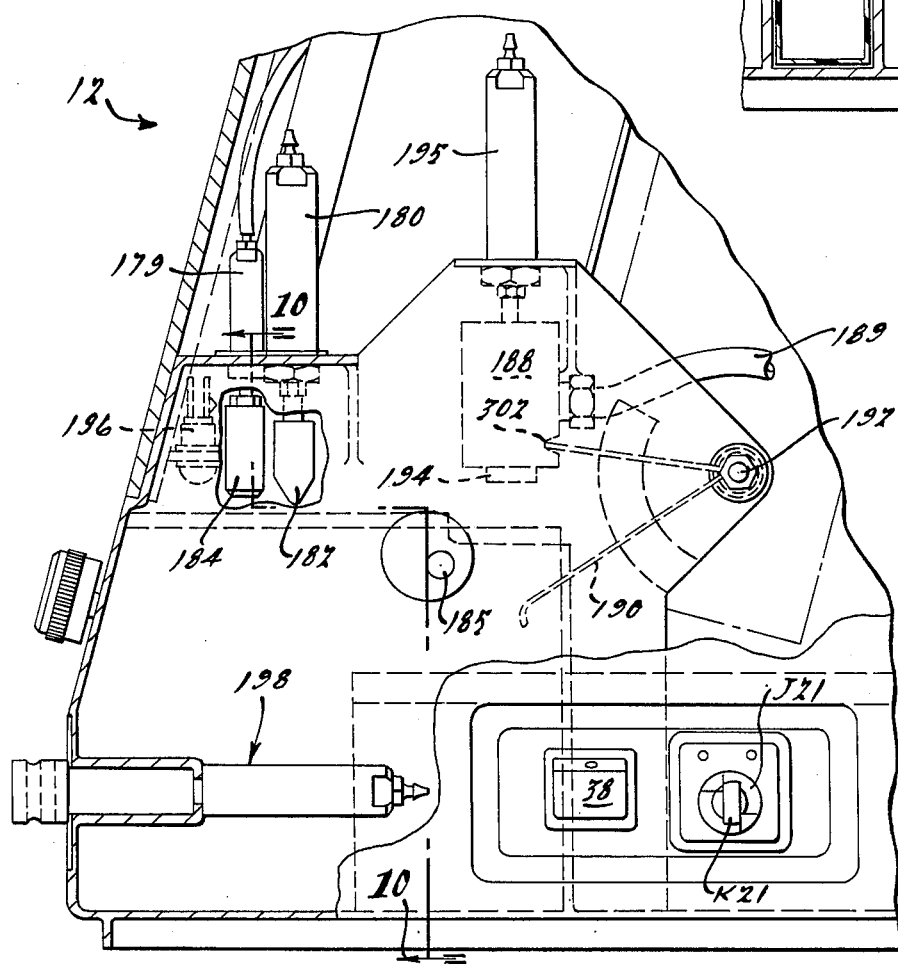

COLLECTION CONTAINER FOR OPHTHALMIC SURGICAL SYSTEM

BACKGROUND AND SUMMARY OF THE INVENTION

The present invention relates generally to microsurgical and ophthalmic systems and more particularly to an ophthalmic system employing a vacuum-operated aspiration system with a removable fluid collection cassette having reusable and disposable components and adapted for use with an optically sensed fluid level shutoff system.

In aspirating fluids and tissue from the surgical situs, as during eye surgery, it is the present practice to draw the aspiration fluid into a disposable cassette by connecting the aspirating instrument to the cassette and then introducing a vacuum into the cassette using a pump or the like. To gain more precise control over the aspiration suction, the flexible tubing between the aspirating instrument and the cassette is conventionally routed through a pinch valve arrangement which squeezes the tubing in response to a remote control mechanism (typically a foot pedal) operated by the surgeon.

In order to ensure that the aspirating vacuum changes quickly in response to the surgeon's control, some conventional cassettes employ a reduced volume primary collection canister with means for periodically emptying the primary canister into a larger secondary canister. Relatively complex tubular systems, valves and often several vacuum sources are required to implement such systems. Aside from adding to the complexity of the ophthalmic system, the additional tubing, valves and pumps represents considerable additional expense. This is particularly true in the case of present day ophthalmic cassettes which are designed to be discarded after a single use.

The ophthalmic cassette of the present invention offers much improvement over the present day state of the art. The inventive cassette greatly simplifies the interconnecting tubing and valving arrangements needed for precise control of the aspiration suction. This is accomplished while, at the same time, providing a cassette with reusable components, thereby saving some of the surgical equipment costs.

Accordingly, the invention provides a microsurgical cassette for use in a vacuum-operated microsurgical system having an aspirating instrument. The cassette comprises a plurality of interconnected vessel walls forming a fluid containment vessel having an interior. One of the vessel walls defines a recess which has a first wall portion in common with the vessel interior. An aspiration port is disposed in the first wall portion so that it communicates between the recess and the vessel interior. A vacuum port is disposed on one of the vessel walls and communicates with the vessel interior, for introducing a vacuum into the interior by connection to a vacuum pump, for example. The fluid containment vessel comprises an autoclavable plastic material capable of being sterilized and reused.

The invention further comprises a reusable coupler member of a size and shape for removable frictional fit within the recess. The coupler member has a first nipple for insertion and communication with the aspiration port. The coupler has a second nipple for communicating with an external aspirating instrument of the microsurgical system. The coupler has an internal passageway which extends and communicates between the first and second nipples and at least a portion of the coupler through which the passageway extends is made of a resilient and deformable plastic material. Deformation of the coupler portion is capable of closing the passageway and thereby controlling aspiration of fluid and tissue from the surgical situs.

The second nipple includes an elongated end portion and an intermediate portion which has a structurally weakened breakaway section for severing the elongated end portion from the remainder of the second nipple. The second nipple is insertable through an opening in the recess, which opening communicates with the exterior of the cassette for connection to the external aspirating instrument through a flexible tubing, for example. During the installation of the reusable coupler, this elongated end is inserted through the recess opening and is manually pulled through the opening to assist in seating the coupler in the recess. Further pulling on the elongated end portion causes it to break away from the remainder of the second nipple, leaving the second nipple properly positioned within the opening through the recess. Once the elongated end portion has been broken away in this fashion, the assembled cassette is ready to use.

The coupler member has a generally I-shaped body portion with enlarged end portions for frictional fit within the recess, leaving the middle portion free for grasping with the fingertips when removing the coupler from the recess. The coupler member is also formed to provide a reflux chamber, and a tube may also be connected to the coupler member to carry the aspirant to the bottom of the cassette.

BRIEF DESCRIPTION OF THE DRAWINGS

FIG. 4 is a side elevational view of the cassette of the invention;

FIG. 4A is a partial side elevation view showing an alternative float assembly according to the present invention;

FIG. 5 is a top view of the cassette of FIG. 4;

FIG. 6 is a right end view of the cassette of FIG. 4;

FIG. 9 is a cross-sectional view through the system console; and

FIG. 10 is a partial cross-sectional view taken along the line 10-10 in FIG. 9, illustrating the level sensors of the invention.

DESCRIPTION OF THE PREFERRED EMBODIMENT

Figure 1:
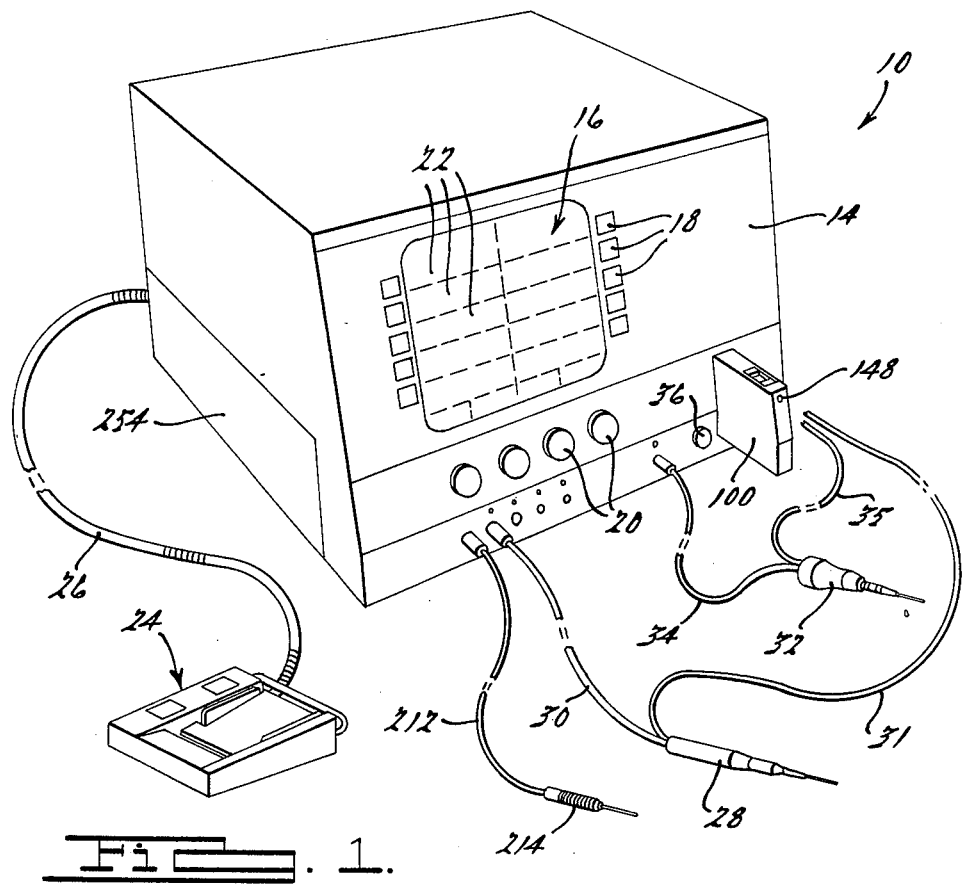
FIG. 1 is a perspective view of the microsurgical system console of the invention.
Figure 2:
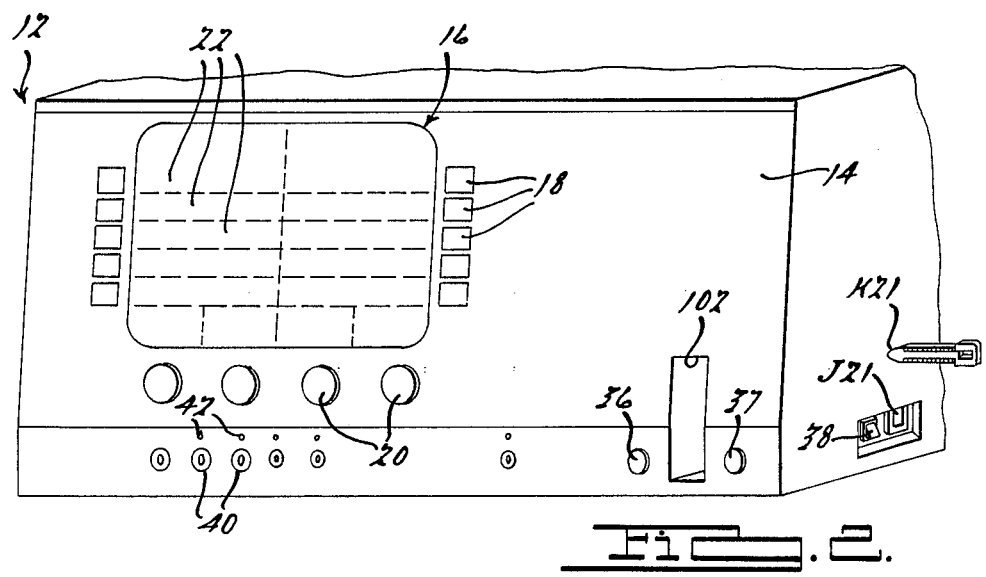
FIG. 2 is a front view of the system console showing the front panel layout in greater detail.

Referring first to FIGS. 1 and 2, a microsurgical control system 10 is provided having a foot pedal assembly 24 according to the present invention. The control system 10 includes a system console 12 which has an upwardly and inwardly sloping front panel 14 and at least one removable access door 254 in one of the side panels. On the front panel 14 is an electronic display screen 16, a plurality of push button switches or touch sensitive pads 18 and a plurality of "endless" digital potentiometer knobs 20. The push buttons 18 and knobs 20 are actuable by the surgeon or nurse to select various different modes of operations and functions used in various surgical procedures.

The console 12 also includes a cassette eject button 36, an irrigation pinch valve 37, and a power on/off switch 38.

The electronic display screen 16 is controlled by a computer to provide one or more different menus or messages which instruct the operator as to the function of the buttons 18 and knobs 20 for the particular mode selected. The display screen 16 may be conceptually divided into display screen regions 22 with the buttons 18 and knobs 20 being positioned at locations around the periphery of the screen 16 corresponding to the regions 22. By virtue of the location of the buttons 18 and knobs 20 adjacent the screen 16, for example, a message in the upper left-hand corner of the screen 16 is readily understood by the operator as referring to the upper left most button. This arrangement allows the indicated function of each button 18 and knob 20 to be readily changed. The use of an electronic display screen 16 also permits the buttons 18 and knobs 20 to be labeled in virtually any language.

The microsurgical control system 10 is adapted for use with a number of different surgical instruments. As shown in FIG. 1, a fiber optic illumination instrument 214 is coupled to the console 12 via fiber optic cable 212. Also illustrated is a fragmentation emulsification instrument 28 coupled to the console 12 through an electrical cable 30. The instrument 28 is also coupled to a collection container or cassette 100 through an aspiration tube 31. A cutting instrument 32 is also shown which is coupled to the console 12 through tubing 34 and to the cassette 100 through tubing 35. The cutting instrument 32 may be a guillotine cutter for vitrectomy procedures, or it may be a microscissors instrument for proportionate and multiple cutting. However, when the microscissors instrument is used, the instrument is not connected to the cassette 100.

While certain microsurgical instruments have been illustrated in FIG. 1, it will be understood that the microsurgical control system 10 can be used with other similarly equipped instruments. In general, any of the microsurgical instruments are actuated or controlled by fluid pressure (positive pressure or negative pressure). However, it should be appreciated that other suitable types of control signals may be used in the appropriate application.

To provide irrigation/aspiration capabilities, the control system 10 further includes the removable cassette 100 which may be inserted into a cassette slot 102 in the console 12. The cassette 100 has a passageway opening 148 to which an aspiration tube from an aspiration instrument may be connected. The console 12 also includes a plurality of couplers 40 to which surgical instruments described above may be attached. Above each coupler 40 is a light emitting diode 42 which is illuminated when the instrument connected to the associated coupler 40 is activated. To store the operating parameters of a particular microsurgical operation, the control system 10 electrically communicates with a digitally encoded memory key K21. The memory key K21 includes an integrated memory circuit which stores the operating parameters for a particular surgical procedure. The console 12 receives the key K21 through a slot J21. Suitable types of memory keys K21 are commercially manufactured by Data Key Inc., Burnsville, Minn. However, it should be appreciated that other suitable means for accessing specifically assigned memory locations may be used in the appropriate application.

A further description of the control system may also be found in the following commonly owned patent applications which were filed on even date herewith, and which are hereby incorporated by reference: Scheller, et al U.S. patent application Ser. No. 928,170 filed Nov. 6, 1986, entitled "Control System For Ophthalmic Surgical Instruments"; Scheller, et al U.S. patent application Ser. No. 927,827 filed Nov. 6, 1986, entitled "Illumination System For Fiber Optic Lighting Instruments"; and Scheller U.S. patent application Ser. No. 927,807 filed Nov. 6, 1986, entitled "Foot Pedal Assembly For Ophthalmic Surgical Instrument".

Having thus described the overall microsurgical system, the cassette 100 according to the present invention will now be described in detail. With reference back to FIGS. 1 and 2, it will be recalled that cassette 100 is adapted for slidable insertion into cassette slot 102 on the front panel of the system console. Cassette 100 is shown in a partially inserted position in FIG. 1. When fully inserted for use, the outwardly facing surfaces of cassette 100 are generally flush with the front panel of the system console.

Figure 3:
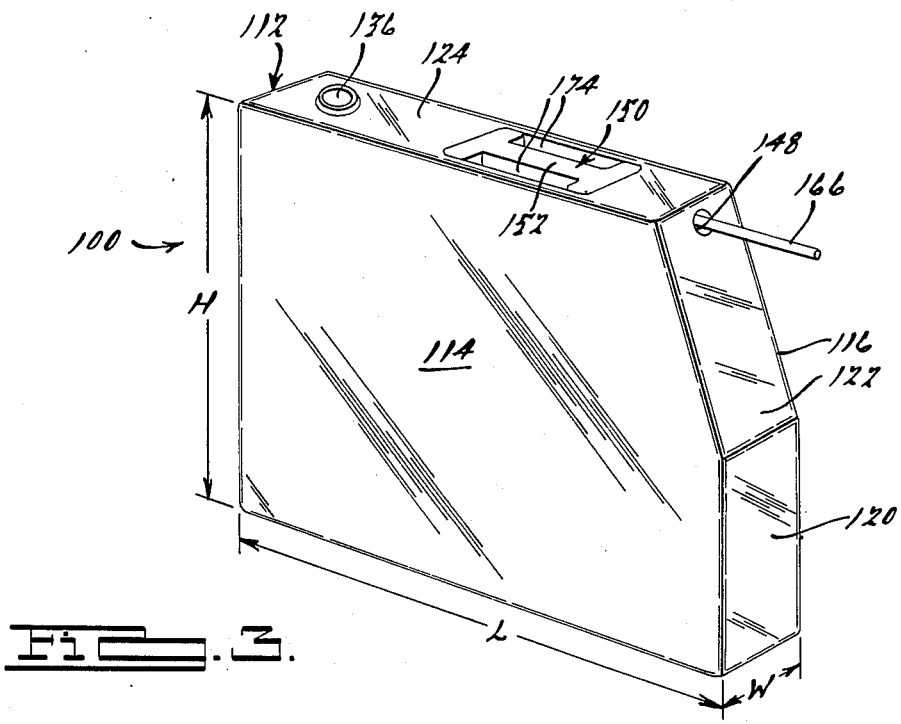
FIG. 3 is a perspective view of the microsurgical cassette of the invention.

Referring now to FIG. 3, cassette 100 comprises a fluid containment vessel 112 which is formed by a plurality of interconnected vessel walls. With additional reference to FIGS. 4 through 6, vessel 112 includes first and second vertically disposed sidewalls 114 and 116, third and fourth vertically disposed sidewalls 118 and 120, angularly disposed sidewall 122, top wall 124 and bottom wall 126. Preferably, the container walls are made of an autoclavable polycarbonate copolymer plastic material such as General Electric Lexan (R) plastic or the like. The plastic material used in constructing the vessel sidewalls is able to withstand the temperatures developed during autoclaving. Preferably, all but the bottom wall are integrally formed as a one-piece molding. Bottom wall 126 is separately fabricated and includes a raised rectangular-shaped flange 128 (FIGS. 4 and 6) which fits inside the open end defined by the vertical sidewalls to form a fluid tight seal when the bottom wall is ultrasonically welded in place.

Top wall 124 is provided with an integrally formed recess 130. Preferably, recess 130 is rectangular in shape and includes a first wall portion 132 which is in common with the interior 134 of vessel 112. Top wall 124 is also provided with a vacuum port 136 which opens into and communicates with the interior 134. In a similar fashion, the first wall portion 132 of recess 130 is provided with an aspiration port 138, which likewise opens into and communicates with the interior 134 of vessel 112. Preferably, aspiration port 138 is provided with a short extension tube 140 leading into the interior 134.

Recess 130 further includes a second wall portion 142 which defines an opening 144 into a horizontally disposed passageway 146. Passageway 146 opens in angularly disposed sidewall 122 to provide an aperture 148 for connecting the external aspirating instrument. Preferably, passageway 146 is integrally formed in the top wall 124 with a portion of the material forming the passageway being disposed within interior 134. In this fashion, the passageway 146 lies generally beneath the surface of the top wall, leaving the top wall surface unobstructed to allow the cassette to be slid into cassette slot 102 during use. At the same time, the top wall serves to cover passageway 146 to thereby capture the fluid conduits inserted therethrough, as will be discussed more fully below.

As perhaps best seen in the drawings, vessel 112 has three orthogonal average dimensions, a width "W," length "L" and a height "H" (shown in FIG. 3). These dimensions are described as average dimensions, since by virtue of the angularly disposed side wall 122, the lengthwise dimension "L" varies in accordance with height. Nevertheless, the width dimension "W" which characterizes the spacing between sidewalls 114 and 116, is the smallest of the three orthogonal average dimensions. In the presently preferred embodiment, the width dimension "W" is on the order of one inch, the length dimension "L" is on the order of between 4½ and 5 inches (depending upon where measured), and the height dimension "H" is on the order of four inches. It will, of course, be understood that the invention is not intended to be limited to these precise dimensions, and that these dimensions are given merely to provide a better understanding of the relative size and shape of the cassette.

Figure 7:
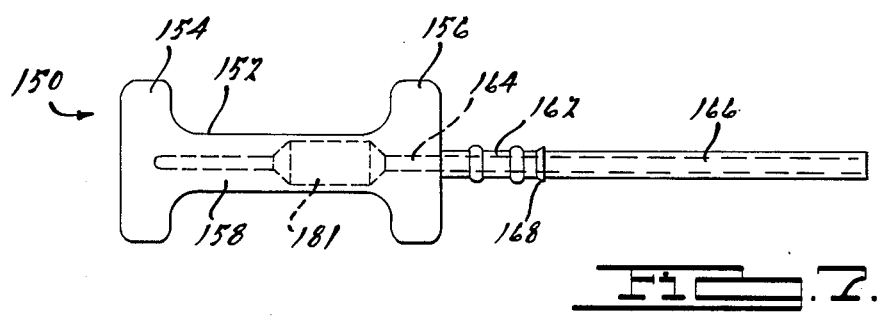
FIG. 7 is a top view of the coupler member of the cassette of FIG. 3.
Figure 8:
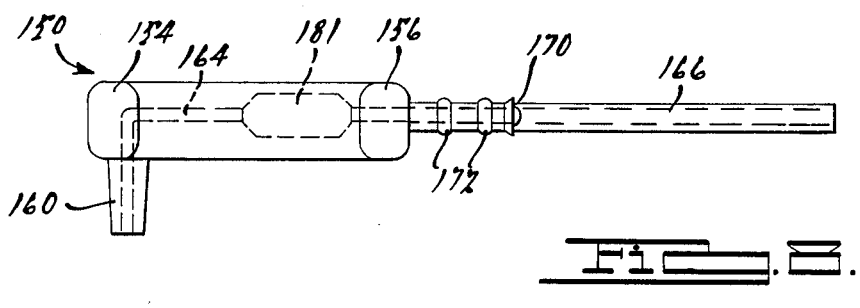
FIG. 8 is a side view of the coupler member of FIG. 7.

In addition to the reusable vessel 112, cassette 100 further includes a reusable coupler member 150, which is shown in position in FIG. 3 and shown in detail in FIGS. 7 and 8. Coupler member 150 has an I-shaped body portion 152 having first and second enlarged end portions 154 and 156 and an elongated middle portion 158. Integrally formed at end portion 154 is a first nipple 160 which extends generally at right angles to the middle portion 158. Integrally formed at end portion 156 is a second nipple 162, which extends longitudinally outwardly in line with the middle portion 158. First and second nipples 160 and 162 are thus generally perpendicular to one another.

Coupler member 150 has integrally formed therein an internal passageway 164 which extends between and communicates between the first and second nipples. Second nipple 162 includes an elongated end portion 166 and a structurally weakened breakaway intermediate portion 168.

Intermediate portion 168 is provided with perforations as at 170 which structurally weaken that portion of the second nipple to allow the elongated end portion 166 to be torn, severed or pulled away from the remainder of the second nipple. Preferably, the remaining portion of the second nipple 162 is provided with a pair of integrally formed annular sealing rings 172.

The overall size and shape of the I-shaped body 152 is such that it frictionally fits within and is captured within recess 130. More specifically, end portions 154 and 156 fit within the four corners of recess 130, leaving the middle portion 158 as a means for manually grasping the coupler member 150 to remove it from the recess after use. As illustrated in FIG. 3, the middle portion has a transverse dimension less than the corresponding dimension of the recess, so that the coupler member fills less than the entire volume of the recess to thereby define a pair of unfilled spaces 174 which may be reached into with fingertips to manually grasp and remove the coupler member.

As will be explained below, in use the middle portion of the coupler member is positioned beneath a solenoid actuator 180 (FIG. 9) which pinches the middle portion against the wall portion 132 of recess 130, thereby closing or partially closing passageway 164. The unfilled spaces 174 also serve to allow the pinched middle portion to flatten outwardly to allow the pinching action to take place.

The middle portion at the coupler member 150 is also positioned beneath a reflux actuator 179 which pinches a reflux chamber portion 181 at the coupler member. In operation, the wedge shaped plunger 182 of the solenoid actuator 180 will pinch off the passageway 164 before the plunger 184 of the reflux actuator squeezes the reflux chamber 181 to push a small amount of fluid back out the passageway at the nipple 162. When aspiration is again desired, the solenoid plunger 182 is withdrawn first before releasing the reflux plunger 184.

Although a variety of materials may be used, the presently preferred coupler member is molded from an elastomeric, resilient and deformable plastic material, such as a silicone polymer or polysiloxane polymer, or the like.

Referring now to FIGS. 9 and 10, the solenoid actuator and vacuum port connection within system console 10 will now be described. Positioned within console 10 generally above the cassette slot 102 are the solenoid actuator 180 and the reflux actuator 179. When cassette 100 is fully inserted in slot 102, this solenoid actuator is positioned directly above the middle portion 158 of coupler member 150. The actuator, when energized, pinches the middle portion 158 against the first wall portion 132 of the cassette, causing the internal passageway 164 to be fully blocked. In the appropriate application, the solenoid actuator 180 could be pulsed with a duty cycle which would control the aspiration flow, as opposed to the aspiration pressure.

In order to determine when the cassette has a full fluid level or is nearly full, a level sensor 185 is provided. The sensor comprises an infrared light emitting diode 185a and phototransistor pair 185b. The emitter may be MEK730 Gallium arsenide diodes and the phototransistor may be MTH320 silicon phototransistors. When the level of fluid in the container rises to a point where it blocks or partially blocks the light being communicated between the light emitting diode and phototransistor pair, a control signal is generated. This signal is sensed by the master computer control system. It should be appreciated that another sensor could be positioned lower than sensor 185 to provide an early warning that the cassette is nearing a full condition. In the appropriate application, the sensor 185 might also be able to detect the meniscus of the fluid level as well.

In order to supply the aspiration vacuum to cassette 100, movable vacuum coupler 188 is provided. The coupler 188 is connected to the vacuum venturi of the control console 12 via tube 189. Associated with coupler 188 is a sensor arm 190 which is physically contacted by the third vertical sidewall 118 of the cassette during insertion. Arm 190 is pivotal about pivot 192 and is also connected to the vacuum source as at 302. The arm 190 provides a cassette ejection spring for the control console 12. The act of inserting cassette 100 trips a limit switch (not shown) which actuates the pneumatic circuit connected to cylinder 195 and causes the vacuum coupler 188 to move downwardly so that the elastomeric connection nipple 194 mates and seals with the vacuum port 136 of the cassette.

FIG. 9 also shows a cassette illumination lamp 196 situated above the cassette 100, and an irrigation pinch valve 198 disposed off to the side. The pinch valve 198 includes a pneumatically operated plunger for selectively blocking off the flow of irrigation fluid. It should also be noted that the spring arm 190 is mounted for rotation in response to the movement of the coupler 188. This rotation prevents the spring arm 190 from working against the coupler 188 which acts as a capture block for the cassette 100. Additionally, while any suitable vacuum and/or pressure source may be used in the console 12 for the pneumatically operated devices described above, it is preferred that compressed air be employed. With the use of compressed air, a suitable venturi arrangement can be employed to create the vacuum necessary for purposes of aspiration.

In order to assemble coupler member 150 in the cassette 100, coupler member 150 is inserted into recess 130 by first inserting the elongated end portion 166 through opening 144 and passageway 146 so that it protrudes outwardly from aperture 148. At the same time, the first nipple 160 is aligned with aspiration port 138, with the nipple being inserted into the port. As these two actions are being accomplished, the I-shaped body portion 152 is inserted in the recess 130 until the top surface of the coupler member 150 lies generally flush with the plane of top wall 124. Due to the elastomeric properties of the coupler member, a tight frictional fit results. Once the coupler member 150 is in place, additional pulling force is exerted on the elongated end portion 166 until it breaks away at the intermediate portion 168. The act of breaking off the end 166 also acts to firmly seat the sealing rings 172 in passageway 146. The cassette 100 is now ready for use and may now be inserted into the cassette slot 102 on the system console.

Referring again to FIGS. 4 and 6, a float assembly 200 is shown to be welded or glued to the top wall 124 of the cassette 100. This float assembly may be used to facilitate the operation of the level sensor 185. Specifically, the float assembly includes a channel-shaped enclosure member 202 and a float ball 204. The width of the enclosure member 202 is less than "W" so that the fluid in the cassette will be able to raise the ball and interfere with the transmission of light across the sensor. FIG. 4A shows an alternative float assembly 206 whose enclosure walls 208-210 may be integrally molded with the cassette 100. The bottom wall 212 of the enclosure may then be welded or glued to the walls 208-210 in order to trap the ball 214 within the enclosure. FIGS. 4 and 6 also show a tube 216 which can be connected to the coupler 150 in order to direct the flow of aspirant to the bottom of the cassette 100.

While the invention has been described in connection with its presently preferred embodiment, it will be understood that the invention is capable of certain modification and change without departing from the spirit of the invention as set forth in the appended claims.

What is claimed is:

1. A microsurgical cassette for use in a vacuum operated microsurgical system having an aspirating instrument, comprising:
   a plurality of interconnected vessel walls forming a fluid containment vessel having an interior;
   an aspiration port disposed in a first wall portion and communicating between said wall portion and said vessel interior;
   a vaccum port disposed in one of said vessel walls and communicating with said vessel interior for introducing a vacuum into said interior;
   a coupler member having a first means for communicatiang with said aspiration port and having a second means for communicating with said aspirating instrument of said microsurgical system;
   said coupler member having an internal passageway extending and communicating between said first and second means;
   at least a portion of said coupler member through which said passageway extends being made of a resilient and deformable plastic material, the deformation of said coupler portion being capable of closing said passageway and thereby controlling the flow of aspiration fluid; and
   wherein one of said vessel walls defines a recess which extends below the plane of said one vessel wall and said coupler member has a top surface which lies generally flush with the plane of said one vessel wall, when said coupler member is fit within said recess.

2. The cassette of claim 1 wherein said vessel walls are made of autoclavable plastic material.

3. The cassette of claim 1 wherein said vessel walls are made of a polycarbonate material.

4. The cassette of claim 1 wherein said coupler member means is made of a silicone polymer.

5. The cassette of claim 1 wherein said coupler member means is formed to include a reflux chamber in said passageway.

6. The cassette of claim 1 wherein both said vacuum port and said aspiration port are disposed on the same one of said vessel walls.

7. The cassette of claim 1 wherein one of said vessel walls is a top wall and said vacuum port and said aspiration port are disposed on said top wall.

8. The cassette of claim 1 wherein said recess has a second wall portion which defines an opening for receiving said second means.

9. The cassette of claim 1 wherein said first and second means are disposed generally at right angles to one another.

10. The cassette of claim 1 wherein said second means includes an elongated end portion and an intermediate portion, said intermediate portion having structurally weakened breakaway means for severing said elongated end portion from the remainder of said second means.

11. The cassette of claim 1 wherein said second means includes at least one annular sealing means around the circumference thereof.

12. The cassette of claim 1 wherein said vessel walls include at least one pair of generally parallel and vertically disposed sidewalls of a light transmissive material.

13. The cassette of claim 12 wherein said vessel has three orthogonal average dimensions and said vertically disposed sidewalls are spaced apart a distance which defines the smallest of said three orthogonal average dimensions.

14. A microsurgical cassette for use in a vacuum operated microsurgical system having an aspirating instrument, comprising:
   a plurality of interconnected vessel walls forming a fluid containment vessel having an interior;
   an aspiration port disposed in a first wall portion and communicating between said wall portion and said vessel interior;
   a vacuum port disposed in one of said vessel walls and communicating with said vessel interior for introducing a vacuum into said interior;
   a coupler member having a first means for communicating with said aspiration port and having a second means for communicating with said aspirating instrument of said microsurgical system;

chamber means in the fluid containment vessel and float means movably located within the chamber means operative to rise in the chamber means toward the top of one of the vessel walls whenever fluid in the vessel reaches a predetermined level;

said coupler member having an internal passageway extending and communicating between said first and second means; and at least a portion of said coupler member through which said passageway extends being made of a resilient and deformable plastic material, the deformation of said coupler member portion being capable of closig said passageway and thereby controlling the flow of aspiration fluid.

15. The cassette of claim 14 wherein the chamber means is integrally formed with said top vessel wall.

16. The cassette of claim 14 wherein said float means comprises a substantially spherical ball.

17. A microsurgical cassette for use in a vacuum operated microsurgical system having an aspirating instrument, comprising, a plurality of interconnected vessel walls forming a fluid containment vessel having an interior;

one of said vessel walls defining a recess which has a first wall portion in common with said vessel interior;

an aspiration port disposed in said first wall portion and communicating between said recess and said vessel interior;

a vacuum port disposed in one of said vessel walls and communicating with said vessel interior for introducing a vacuum into said interior;

a coupler member means having an I-shaped body portion having first and second end portions of a size and shape to frictionally fit within said recess and having an elongated middle portion between said end portions of a transverse dimension less than the corresponding dimension of said recess, the middle portion thereby providing a means for manually grasping said coupler member means to remove it from said recess;

said coupler member means having a first means for communicating with said aspiration port and having a second means for communicating with said aspirating instrument of said microsurgical system;

said coupler means having an internal passageway extending and communicating between said first and second means;

at least a portion of said coupler means through which said passageway extends being made of a resilient and deformable plastic material, the deformation of said coupler means portion being capable of closing said passageway and thereby controlling the flow of aspiration fluid.

18. The cassette of claim 17 wherein said internal passageway extends longitudinally through said middle portion.

19. A microsurgical cassette for use in a vacuum operated microsurgical system having an aspirating instrument, comprising:

a plurality of interconnected vessel walls forming a fluid containment vessel having an interior;

one of said vessel walls defining a recess which has a first wall portion in common with said vessel interior;

an aspiration port disposed in said first wall portion and communicating between said recess and said vessel interior;

a vacuum port disposed in one of said vessel walls and communicating with said vessel interior for introducing a vacuum into said interior;

a coupler member means positioned in said recess such that said coupler member means fills less than the entire volume of said recess to thereby define at least one unfilled space for reaching with the fingertips to grasp and remove said coupler member means from said recess;

said coupler member means having a first means for communicating with said aspiration port and having a second means for communicating with said aspirating instrument of said microsurgical system;

said coupler means having an internal passageway extending and communicating between said first and second means;

at least a portion of said coupler means through which said passageway extends being made of a resilient and deformable plastic material, the deformation of said coupler means portion being capable of closing said passageway and thereby controlling the flow of aspiration fluid.

20. A microsurgical cassette for use in a vacuum operated microsurgical system having an aspirating instrument, comprising:

a plurality of interconnected vessel walls forming a fluid containment vessel having an interior;

one of said vessel walls defining a recess which has a first wall portion in common with said vessel interior;

an aspiration port disposed in said first wall portion and communicating between said recess and said vessel interior;

a vacuum port disposed in one of said vessel walls and communicating with said vessel interior for introducing a vacuum into said interior;

a coupler member positioned in said recess;

said coupler member having a first means for communicating with said aspiration port and having a second means for communicating with said aspirating instrument of said microsurgical system;

said coupler having an internal passageway extending and communicating between said first and second means;

at least a portion of said coupler through which said passageway extends being made of a resilient and deformable plastic material, the deformation of said coupler portion being capable of closing said passageway and thereby controlling the flow of aspiration fluid.

21. A microsurgical cassette for use in a vacuum operated microsurgical system having an aspirating instrument, comprising:

a plurality of interconnected vessel walls forming a fluid containment vessel having an interior;

an aspiration port disposed in a first wall portion and communicating between said wall portion and said vessel interior;

a vacuum port disposed in one of said vessel walls and communicating with said vessel interior for introducing a vacuum into said interior;

a coupler member having a first means for communicating with said aspiration port and having a second means for communicating with said aspirating instrument of said microsurgical system;

said coupler having an internal passageway extending and communicating between said first and second means;

at least a portion of said coupler through which said passageway extends being made a resilient and deformable plastic material, the deformation of said coupler portion being capable of closing said passageway and thereby controlling the flow of aspiration fluid; and wherein said second means includes an elongated end portion and an intermediate portion, said intermediate portion having structurally weakened breakaway means for severing said elongated end portion from the remainder of said second means.

* * * * *

UNITED STATES PATENT AND TRADEMARK OFFICE
CERTIFICATE OF CORRECTION

PATENT NO. : 4,773,897

DATED : September 27, 1988

INVENTOR(S) : Gregg Scheller et al

It is certified that error appears in the above-identified patent and that said Letters Patent is hereby corrected as shown below:

| | |
|---|---|
| Column 2, line 25, | "to" should be --for--. |
| Column 4, line 37, | "polycarborate" should be --polycarbonate--. |
| Column 5, line 8, | insert "as" before --shown--. |
| Column 8, line 21, | delete "means" after --member--. |
| Column 8, line 23, | delete "means" after --member--. |
| Column 9, line 13, | "closig" should be --closing--. |
| Column 9, line 21, | "," should be --:--. |
| Column 11, line 2, | "of" should be inserted after --made--. |

Signed and Sealed this
Fourteenth Day of November, 1989

Attest:

JEFFREY M. SAMUELS

*Attesting Officer*      *Acting Commissioner of Patents and Trademarks*